United States Patent [19]

Maumenee et al.

[11] Patent Number: 4,866,049

[45] Date of Patent: Sep. 12, 1989

[54] OPHTHALMIC COMPOSITION AND METHOD OF USING SAME

[75] Inventors: A. Edward Maumenee, Stevenson, Md.; Richard L. Giovanoni, East Taunton, Mass.

[73] Assignee: Spectra Pharmaceutical Services, Inc., Hanover, Mass.

[21] Appl. No.: 83,168

[22] Filed: Aug. 10, 1987

[51] Int. Cl.$^4$ .............................................. A61K 31/56
[52] U.S. Cl. ..................................... 514/169; 514/170; 514/171; 514/172; 514/173; 514/174; 514/175; 514/180; 514/181; 514/182; 514/912
[58] Field of Search ............... 514/169, 170, 171, 172, 514/173, 174, 175, 180, 181, 182, 912

[56] References Cited

U.S. PATENT DOCUMENTS

| | | | |
|---|---|---|---|
| 4,093,973 | 4/1978 | van der Vies | 514/170 |
| 4,478,818 | 10/1984 | Shell et al. | 514/171 |
| 4,496,554 | 1/1985 | Wong | 514/179 |
| 4,649,047 | 10/1987 | Kaswan | 514/914 |
| 4,686,214 | 8/1987 | Boltralik | 514/177 |

Primary Examiner—William R. Dixon, Jr.
Assistant Examiner—Margaret B. Medley
Attorney, Agent, or Firm—Watson, Cole, Grindle & Watson

[57] ABSTRACT

The present invention relates to ophthalmic compositions and their preparation and use. More specifically, the invention relates to ophthalmic compositions useful in the treatment of surface disorders of the eye caused by abnormal precorneal tear film, and most specifically to the compositions for treatment of so-called dry eye conditions.

20 Claims, No Drawings

OPHTHALMIC COMPOSITIONN AND METHOD OF USING SAME

BACKGROUND OF THE INVENTION

In the human eye, a stable precorneal tear film is essential for maintenance of a healthy and comfortable ocular surface. Any breakdown in the precorneal tear film can result in symptoms of dryness, grittiness, irritation, burning, redness, itching, blurred vision, and photophobia in the eye, any of which may result in damage to both the cornea and conjunctiva.

The precorneal tear film is composed of three layers, the inner layer immediately adjacent to the ocular surface being a thin layer of mucin about 0.02 microns thick which is derived from goblet cells located in the conjunctiva. The intermediate layer is an aqueous layer about 7.0 microns thick which is derived from the lacrimal gland and from the accessory lacrimal gland and from the accessory lacrimal glands of Wolfring and Krause. The outermost layer is a layer of lipids about 0.1 microns thick which are derived from the meibomian glands lining the upper and lower eye lid margins. The meibomian glands continuously produce meibum material composed of numerous different types of lipids and the glands excrete the material onto the eyelid margin. The process of blinking spreads these lipids of the meibum material uniformly over the ocular surface to form the outer portion of the precorneal tear film.

Several different diseases can affect various portions of the precorneal tear film. For example, the Stevenss-Johnson syndrome can cause loss of goblet cells in the conjunctiva thereby resulting in the loss of the mucin layer. As a consequence, the tear film becomes extremely unstable and the resultant changes in the ocular surface may be severe. Similarly, keratoconjunctivitis sicca is loss of the aqueous component of the precorneal tear film, which results in profound drying changes on the ocular surface. Impairment of the secretion from meibomian glands also alters the stability of the precorneal tear film such that severe damage to the ocular surface through drying can result.

Meibum material primarily performs three functions in the eye. First, the material provides the lipids for the outermost layer of the precorneal tear film, which gives stability to the tear film. Second, meibum material retards evaporation of the aqueous phase of the precorneal tear film. Finally, meibum coats the lid margins, preventing the development of chronic irritation along the skin of the lids from constant wetting and drying from the aqueous tears. When the meibum content in the tear film is decreased, these functions may not be adequately performed by the remaining meibum. Specifically, break-up time of the precorneal tear film is increased, evaporation of the aqueous phase of the tear film is more rapid, and chronic irritation of the lid margins occurs.

The effects of decreased meibum can be best observed in those patients suffering from congenital ectodermal dysplasia, a rare abnormality which is associated with multiple developmental anomalies including partial or total absence of the meibomian glands. The resultant lack of meibum in the eyes of such patients causes an immediate break-up of the tear film, which results in severe changes of the ocular surface, including opacification of the cornea.

Another example of the lack of meibum is evident in patients suffering from chronic blepharitis, a fairly common condition, especially among the elderly. This condition is characterized by diffuse inflammation around the meibomian gland orifices due to lipid secretions solidifying within the glands, resulting in plugging of the orifices, with gland dilation and distortion. The lid margins becomes thickened and irregular, with dilated blood vessels. Tarsal injection with papillary hypertrophy, bulbar injection and superficial punctate keratopathy (SPK) frequently occur. The latter is attributed to an unstable tear film which is seen clinically by a rapid break-up time of the tear film. These changes in the tear film produce symptoms of burning, irritation, drying, grittiness and the like, as well as changes in visual acuity. The rapid break-up time may be neutralized by expressing fresh meibum from deep within the gland into the tear film.

As set forth above, the condition of meibomian gland dysfunction and its associated symptoms have been recognized for some time. Various treatments have been practiced over the years, present therapy primarily consisting of treatment of the lid margin disease through lid hygiene, and occasional use of antibiotic or steroid ointments, and oral tetracycline antibiotics. Symptoms of the disease are treated through various agents used for the supplementation of aqueous tears. In addition, ointments are often used that act primarily as sealants to the aqueous tear film. These ointments are usually composed of long-chain hydrocarbon products. However, long-chain hydrocarbons do not layer out in the precorneal tear film in a manner similar to meibum, and as a consequence, can cause severe blurring of vision. Thus, they can only be used when visual acuity is not of particular concern. Other treatments have included the frequent use of isotonic or hypotonic buffered saline, the application of viscoelastic materials, and the use of peanut oil.

It is, therefore, the primary object of the present invention to provide an improved ophthalmic composition and method for using same in the treatment in mammals of symptoms of meibomian gland dysfunction where insufficient meibum is produced, and thereby to restore the eye to a condition approximating that when sufficient meibum is produced.

SUMMARY OF THE INVENTION

Briefly, the present invention comprises an ophthalmic composition and method for applying it for the alleviation of symptoms of meibomian gland dysfunction in the eyes of mammals. The compositions comprise therapeutically effective amounts of a mixture of sterol esters, mono and/or di-ester waxes, polar lipids, and a carrier therefor. In approximate quantities by weight, the sterol esters are present in about 20 to 40%, the mono and/or di-ester waxes about 30 to 50% and the polar lipids about 10 to 20%. Even more preferably, the range of sterol esters is 25 to 35%, mono and/or di-ester waxes—40 to 50%, and polar lipids—13 to 16%.

It has been found preferable to utilize both mono and di-ester waxes rather than simply mono or di-ester waxes. When both waxes are utilized, a general, preferred formulation is a composition composed of the following, approximate amounts: sterol esters—20 to 40%; mono-ester waxes—30 to 40%; di-ester waxes—5 to 10%; and polar lipids—10 to 20%.

Certain esters, waxes and lipids have been found preferable for use because of their effectiveness and ease of availability. Thus, the sterol esters may be selected from the group consisting of n-carbon chains of C 12:0 to C 26:0, iso-carbon chains of C 13:0 to C 28:0, and anteiso-carbon chains of C 13:0 to C 29:0. The mono and di-ester waxes are preferably comprised of n-carbon chains of C 12:0 to C 20:0; iso-carbon chains of C 13:0 to C 26:0, and anteiso-carbon chains of C 13:0 to C 27:0.

The ophthalmic ointment that is the subject of the present invention may also advantageously contain other ingredients, e.g., triacylglycerols with carbon chains of about C 12:0 to C 28:0, sterols, fatty acids, preferably with carbon chains of about C 12:0 to C 26:0, and ancillary ingredients to stabilize the mixture, improve dispersion or solubility, and prolong shelf life thereof. When used, these additional materials will ordinarily not be present in amounts in excess of 5% by weight of a total composition.

In actual use, the method of the invention consists of applying the ointment described hereinbefore directly to the eyelid margins, with some pentration directly on the aqueous layer overlying the eye being desirable. In any case, the ointment described, if applied to the upper and lower lid margins, will be spread over the precorneal tear film by blinking, and thereby effectively serve as a meibum substitute in instances where there has been meibum gland dysfunction.

These and other objects, features and advantages of the present invention will become more fully apparent from a consideration of the invention as it is set forth by reference to the following detailed description of preferred embodiments thereof.

DETAILED DESCRIPTION OF PREFERRED EMBODIMENTS

One preferred embodiment of my invention includes sterol esters, by which term I mean to include both esters and alcohols prior to esterification. Examples of such esters are as follows: myristyl alcohol, cetyl alcohol, duodecyl acetate, 2,3-dimethylbutyl-3,7-dimethyl-5-ethyl duodecate, decylbutyl acetate, 1,5-diethy1,3-methylhexyl decate, duodecylbutyl acetate, 3,5-diethyloctanoate-5,propyl decyloctate, decylpentyl pentate, 4-butyl,5,6-dimethyl decyldecate, and combinations thereof. Of these materials, myristyl alcohol and cetyl alcohol are presently preferred because of their ready availability.

With regard to the mono-ester and di-ester waxes of the present invention, examples thereof are myristyl lactate, myristic acid, myristyl myristate, cetyl lactate, octyldodecyl steararoyl stearate, and combinations thereof. Of these myristyl lactate or cetyl lactate are preferred at this time.

The polar lipids of the present invention are preferably selected from a group consisting of cocamide monoethylacetate, and lecithins in which said lecithins are selected from the group consisting of ovalecithin and vegelecithin, and combinations thereof.

Examples of triacylglycerols are glyceryl tripalmitate and glyceryl tristearate, and combinations thereof. Also useful are compounds consisting of sodium lauryl sulfate, lauric acid, oleic acid, olein, and combinations thereof. Sterols are, exemplarily, eicosatrienoic acid, cholesterol, and cholic acid, with cholesterol being most preferred. As useful free fatty acids, some examples are stearic acid, sodium stearate, isodecyl oleate and linoleic acid, and combinations thereof. Linolenic acid is presently a preferred compound.

Ancillary ingredients to stabilize the mixture, improve dispersion or solubility, and prolong shelflife will advantageously be present, and the final formulation may utilize liposome technology to stabilize the product and enhance product delivery. Some of those materials which may be added for these purposes are the following: linoleamide DEA, glyceryl stearate, purified water, mineral oil, propylene glycol, propylene glycol stearate, Tweens 20, 60, and 80, polyglyceryl-4-oleate, sodium bisulfite, ascorbic acid, and alpha-tocopherols. Of these materials, sodium bisulfite, ascorbic acid and various alpha-tocopherols are preservatives. Compositions such as propylene glycol, sorbitol or polyglyceryl-4-oleate are humectants. Ph buffers such as sodium borate and mono and di-sodium phosphates, or salts such as other alkali metal phosphates, carbonates and acetates may be used. Mechanical buffers or viscosity control agents such as compatible, water-soluble celluose derivatives may be utilized, as are surfactants, exemplarily, those commonly available under the Tween trademark. Compatible biocides may also be used.

The carrier for the active ingredients set forth hereinbefore will vary in accordance with whether the ophthalmic composition is to be applied in a form of an ointment or a solution. Thus, sterile water would preferably be used as the carrier if a solution is desired, in which case the composition would be administered in the form of eye drops or as an eye wash. When the composition is to be applied to the lids of the eye in the form of an ointment, periodic application is made to the lids so that upon blinking, the active ingredients are distributed over the surface of the precorneal tear film. When the composition is to be applied in ointment form, the carrier may be any commonly used material that will not be irritative to the eye, e.g., a mixture of mineral oil and petrolatum in a suitable ratio such as 70% to 30% ratio. The carrier may comprise about 95.0 to 99.5% of the entire ointment.

The concentration of the composition of the present invention in the carrier medium is such that inflammation of the eye will not result from application. Thus, where an aqueous solution to be applied and meibomian gland dysfunction is not acute, 10% by weight of the composition in sterile water may be satisfactory. In other instances it might be advisable to have 50 or 70% of the aqueous carrier be comprised of the composition of the present invention.

Preferred embodiments of compositions according to the present invention as now contemplated are as follows:

EXAMPLE 1

| | |
|---|---|
| Myristyl alcohol | 30% |
| Myristyl lactate | 35% |
| Lauric acid | 5% |
| Octyldodecyl steararoyl stearate | 10% |
| Cholesterol | 2% |
| Linoleic acid | 3% |
| Cocamide monoethylacetate | 14% |
| Preservatives, surfactants, biocides, etc. | 1% |

EXAMPLE 2

| | |
|---|---|
| Cetyl alcohol | 28% |
| Cetyl lactate | 36% |
| Sodium lauryl sulfate | 6% |
| Octyldodecyl steararoyl stearate | 9% |

| -continued | |
|---|---|
| Cholesterol | 3% |
| Stearic acid | 2% |
| Lecithin | 16% |
| Preservatives, surfactants, biocides, etc. | 1% |

While the present invention has been described in conjunction with preferred embodiments thereof, certain alterations and modifications in those preferred embodiments and the descriptions of the invention will be apparent to those skilled in the art. It is desired that all such obvious alterations and modifications be considered within the purview of the invention, the scope of which is to be defined only by the following, appended claims and equivalents thereof.

What is claimed is:

1. An opthalmic composition suitable for application to the eye of a mammal suffering meibomian gland dysfunction, comprising therapeutically effective amounts of a mixture of sterol esters, mono and/or di-ester waxes, polar lipids, and a carrier therefor, said composition having the general properties of and being a substitute for the meibum material normally spread over the ocular surface, so that after its application said composition forms an outer portion of and stabilizes the precorneal tear film of the eye and retards evaporation of the aqueous phase of the tear film when normal secretions of meibum material are inadequate or lacking.

2. An ophthalmic composition as claimed in claim 1, in which said mixture comprises by weight approximately 20 to 40% sterol esters, 30 to 50% mono and/or di-ester waxes, and 10 to 20% polar lipids.

3. An ophthalmic composition as claimed in claim 2, in which said mixture comprises 25 to 35% sterol esters, 40 to 50% mono and/or di-ester waxes, and 13 to 16% polar lipids.

4. An ophthalmic composition as claimed in claim 1, in which said mono-ester waxes and said di-ester waxes are both present, in a ratio of about 4 to 6 parts mono-ester to one part di-ester wax.

5. An ophthalmic composition as claimed in claim 1, in which said mixture also comprises triacylglycerols.

6. An ophthalmic composition as claimed in claim 5, in which said triacylglycerols comprise about 3 to 5% by weight of said composition.

7. An ophthalmic composition as claimed in claim 5, in which said triacylglycerols have carbon chains of about 12 to 28 atoms.

8. An ophthalmic composition as claimed in claim 1, in which said sterol esters are selected from the group consisting of duodecyl acetate and 1,5-diethy1,3-methylhexyl decate, and also comprises myristyl alcohol and cetyl alcohol prior to esterification, and combinations thereof.

9. An ophthalmic composition as claimed in claim 1, in which said mono and di-ester waxes are selected from the group consisting of myristyl lactate, cetyl lactate, myristyl myristate and octyldodecyl steraroyl sterate, and combinations thereof.

10. An ophthalmic composition as claimed in claim 1, in which said polar lipids are selected from the group consisting of cocamide monoethylacetate, and lecithins in which said lercithins are selected from the group consisting of ovalecithin and vegelecithin, and combinations thereof.

11. An ophthalmic composition as claimed in claim 1, further comprising sterols.

12. An ophthalmic composition as claimed in claim 11, in which said sterols are selected from the group consisting of cholesterol and cholic acid, and combinations thereof.

13. An ophthalmic composition as claimed in claim 11, in which said free sterols are present in approximately 2 to 4% by weight of the composition.

14. The method of applying the composition of claim 1 to the eye, comprising utilizing water as the carrier thereof and applying the aqueous mixture to the eye.

15. The method claimed in claim 14, in which said mixture is applied as eye drops.

16. The method claimed in claim 14, in which the mixture is applied as an eye wash.

17. The method of applying the composition of claim 1 to the eye, comprising utilizing a mineral oil-based carrier therefor and applying the so-formed ointment to the eyelids.

18. The method claimed in claim 17, in which said carrier is comprised of about 70% mineral oil and 30% petrolatum.

19. The method claimed in claim 17, in which said carrier comprises about 95.0 to 99.5% of said ointment.

20. An ophthalmic composition as claimed in claim 1 in which said mixture further comprises compounds consisting of sodium lauryl sulfate, lauric acid, oleic acid, olein, and combinations thereof.

* * * * *